US010646628B2

(12) United States Patent
Hensler et al.

(10) Patent No.: US 10,646,628 B2
(45) Date of Patent: *May 12, 2020

(54) ANTI-CLOG SUCTION TIP APPARATUS AND METHODS (71) Applicant: H & M INNOVATIONS, LLC, Wilmington, NC (US)

(72) Inventors: Robert Sean Hensler, Wilmington, NC (US); Thomas James Philpott, Charlotte, NC (US); Daniel Lee Bizzell, Charlotte, NC (US); Michael Starkey, Kent, OH (US); Raeshon Lamont McNeil, Charlotte, NC (US); Juan Carlos Perez, Charlotte, NC (US); Thomas Eric Melin, Wilmington, NC (US); Kenneth D. Ballard, King, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,731

(22) Filed: Jun. 26, 2017

(65) Prior Publication Data

US 2017/0290963 A1    Oct. 12, 2017

Related U.S. Application Data

(63) Continuation of application No. 15/396,526, filed on Dec. 31, 2016, now Pat. No. 9,686,896, which is a (Continued)

(51) Int. Cl.
*A61M 5/00* (2006.01)
*A61M 1/00* (2006.01)
(Continued)

(52) U.S. Cl.
CPC .............. *A61M 1/0078* (2013.01); *A01B 5/00* (2013.01); *A61M 1/008* (2013.01);
(Continued)

(58) Field of Classification Search
CPC ........ A61M 5/00; A61M 25/00; A61M 31/00; A61M 25/16; A61M 39/02; A61M 27/00; A61K 9/02
See application file for complete search history.

(56) References Cited

U.S. PATENT DOCUMENTS 3,958,573 A * 5/1976 Wiley .................... A61C 17/04
                                                         604/267
5,628,733 A * 5/1997 Zinreich ............... A61M 27/00
                                                         604/267

(Continued)

*Primary Examiner* — Tatyana Zalukaeva
*Assistant Examiner* — Ilya Y Treyger
(74) *Attorney, Agent, or Firm* — Chad D Tillman; Tillman Wright, PLLC (57) ABSTRACT

Various forms of anti-clog suction tips apparatus are disclosed. An exemplary anti-clog suction tip apparatus includes a suction tip assembly having a suction tip with a suction opening at a first end thereof for removing debris through suction, a hose attachment portion for attaching the suction tip assembly to a suction source, and an ejection wire channel. The apparatus further includes an ejection wire assembly having an ejection wire extending within the channel and an ejection button integral with or connected to the ejection wire. Applying a force to the ejection button advances the ejection wire through the channel such that an end portion of the ejection wire enters the suction tip and dislodges debris clogging the suction tip. The ejection wire may include an enlarged end portion such as, for example a ball tip. One or more of the components of the apparatus may be single-use and disposable.

17 Claims, 10 Drawing Sheets

Related U.S. Application Data continuation of application No. 14/165,563, filed on Jan. 27, 2014, now Pat. No. 9,533,079, which is a continuation of application No. 13/596,036, filed on Aug. 27, 2012, now Pat. No. 8,636,722, which is a continuation of application No. PCT/US2012/052413, filed on Aug. 25, 2012.

(60) Provisional application No. 61/527,123, filed on Aug. 25, 2011, provisional application No. 61/614,915, filed on Mar. 23, 2012.

(51) Int. Cl.
| | | |
|---|---|---|
| *A01B 5/00* | (2006.01) | |
| *A61M 25/00* | (2006.01) | |
| *A61M 31/00* | (2006.01) | |
| *A61M 25/16* | (2006.01) | |
| *A61M 39/02* | (2006.01) | |
| *A61M 27/00* | (2006.01) | |

(52) U.S. Cl.
CPC ......... *A61M 1/0041* (2013.01); *A61M 1/0047* (2013.01); *A61M 5/00* (2013.01); *A61M 25/00* (2013.01); *A61M 31/00* (2013.01)

(56) References Cited

U.S. PATENT DOCUMENTS

| | | | |
|---|---|---|---|
| 7,993,329 B2 * | 8/2011 | Howell | A61B 17/221 |
| | | | 606/127 |
| 2012/0289941 A1 * | 11/2012 | Salehi | A61C 17/043 |
| | | | 604/540 |

* cited by examiner

ANTI-CLOG SUCTION TIP APPARATUS AND METHODS

The present application hereby incorporates by reference each of: U.S. patent application Ser. No. 14/165,563; U.S. patent application Ser. No. 13/596,036; U.S. patent application publication 2013/0053828; international patent application PCT/US12/52413; U.S. provisional patent application 61/527,123; and U.S. provisional patent application 61/614,915. The disclosures of the provisional applications are contained in the Appendix which further is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to suction tips for use during surgical procedures for the removal of biological debris, such as blood, tissue, and the like, from a surgical site of a patient. More particularly, the present invention relates to suction tips with anti-clogging capabilities for removing biological debris lodged within the suction tips. It is believed that a need exists for improvement in surgical suction tips. This, and other needs, are addressed by one or more aspects of the present invention.

SUMMARY OF THE INVENTION

The present invention includes many aspects and features. Moreover, while many aspects and features relate to, and are described in, the context of vacuum removal of biological debris in a surgical environment, the present invention is not limited to use only in vacuum removal of biological debris in a surgical environment, as will become apparent from the following summaries and detailed descriptions of aspects, features, and one or more embodiments of the present invention.

Accordingly, one aspect of the present invention relates to an anti-clog suction tip apparatus. An exemplary such apparatus includes a suction tip assembly, including a suction tip having a suction opening at a first end thereof for removing debris through suction, a hose attachment portion for attaching the suction tip assembly to a suction source, and an ejection wire channel; and an ejection wire assembly, including an ejection wire disposed within the channel and an ejection button integral with or otherwise connected to the ejection wire. Furthermore, applying a force to the ejection button advances the ejection wire through the ejection wire channel such that an end portion of the ejection wire enters the suction tip. Additionally, the end portion of the ejection wire entering the suction tip expels or dislodges debris in the suction tip through the suction opening.

In a feature of this aspect of the invention, the end portion of the ejection wire includes a ball tip.

In another feature, the suction tip assembly includes a handle.

In still another feature, the suction tip assembly includes a vacuum tunnel opening.

In yet another feature, the ejection wire is inserted into the ejection wire channel through a wire insertion opening.

In a variation of this feature, wire insertion opening is threaded.

In still another feature, the ejection wire assembly further comprises an inner member disposed between the ejection wire and the ejection button, an outer member partially surrounding the inner member, and a biasing spring.

In a variation of this feature, the outer member is threaded.

In another variation, the biasing spring biases the ejection button away from the outer member.

In yet another feature, when dislodging debris in the suction opening, the end portion of the ejection wire preferably does not extend more than 3 millimeters beyond the suction opening. In alternate variations of this feature, the ejection wire does extend more than 3 millimeters.

Another aspect of the present invention relates to an anti-clog suction tip apparatus. An exemplary such apparatus includes a suction tip, an interior of the suction tip defining a suction channel for the removal of debris through suction; and an ejection wire assembly removably attachable to the suction tip and transitionable between a retracted position and an advanced position. Furthermore, in the retracted position, the ejection wire assembly is not disposed within the suction channel, and in the advanced position, the ejection wire assembly is at least partially disposed within the suction channel.

In a feature of this aspect, the ejection wire assembly extends within an area of the suction channel in which a clog exists for dislodging and clearing the clog. The ejection wire assembly may extend to and through a suction opening of the suction tip for dislodging a clog in the suction tip.

In another aspect of the invention, an anti-clog suction tip apparatus comprises a suction tip, an interior of the suction tip defining a suction channel for the removal of debris through suction; and means for clearing debris that clogs the suction tip (which "means for" language is intended to invoke §112, ¶6).

In another aspect, an anti-clog suction tip apparatus comprises a suction tip assembly; and an ejection assembly for ejecting debris when the suction tip becomes clogged.

In another aspect of the invention, an eco-friendly system comprises an anti-clog suction tip apparatus formed from single-use disposable components for use with a body which, when combined with the body, form the anti-clog suction tip apparatus. The body is reusable after autoclaving for sterilization.

In another aspect, a kit comprises disposable components for use with a body of an anti-clog suction tip apparatus which, when combined with the body, form an anti-clog suction tip apparatus. In this respect, at least the body is reusable, and additional components of the anti-clog suction tip apparatus that are not part of the kit also are reusable. The body and reusable parts preferably are autoclaved before reuse.

Another aspect of the present invention relates to a method of clearing biological debris from a surgical site. An exemplary such method includes providing a suction tip apparatus, including an interior defining a suction channel, an ejection wire not disposed within the suction channel, and an ejection button; attaching the suction tip apparatus to a suction source; activating the suction source to create a vacuum force in the suction tip apparatus; placing the suction tip apparatus near the debris; causing the vacuum force to pull the debris into the suction tip apparatus; applying force to the ejection button, causing a tip of the ejection wire to enter the suction channel; and dislodging, via the tip of the ejection wire, debris clogging the suction channel.

Additional aspects of the present invention include apparatus and methods for dislodging biological debris clogged in a suction tip, as substantially shown and described herein and in the drawings. Additional features thereof are also shown an described herein and in the drawings.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6 in the United States, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Figure 1:
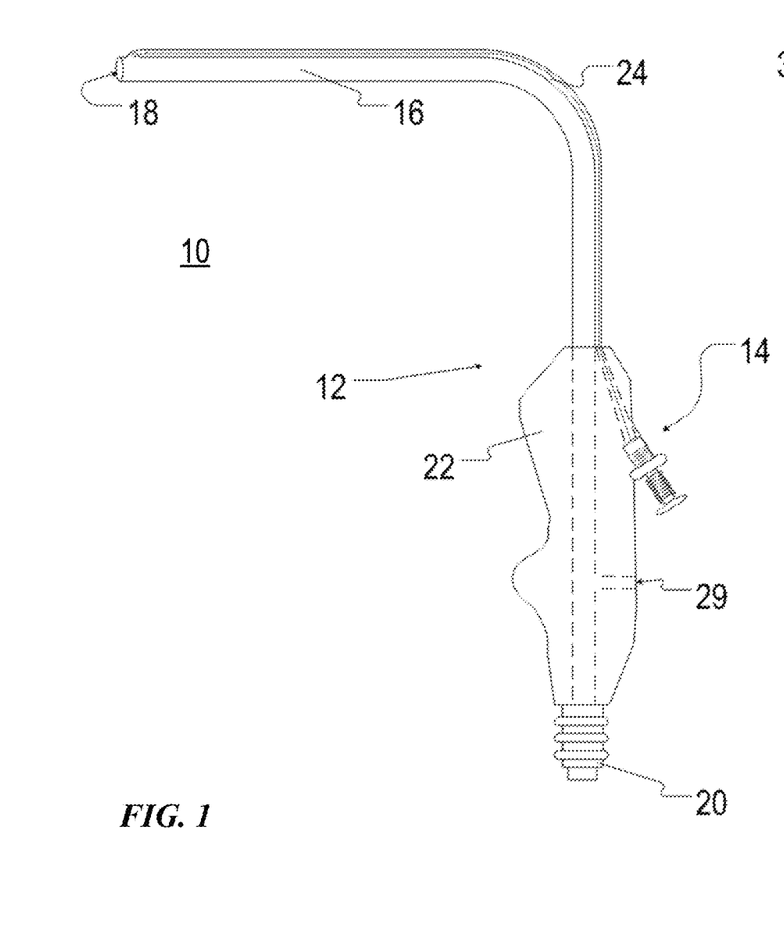
FIG. 1 is a schematic illustration of a side view of a preferred anti-clog suction tip apparatus 10 in accordance with one or more aspects of the invention.
Figure 2:
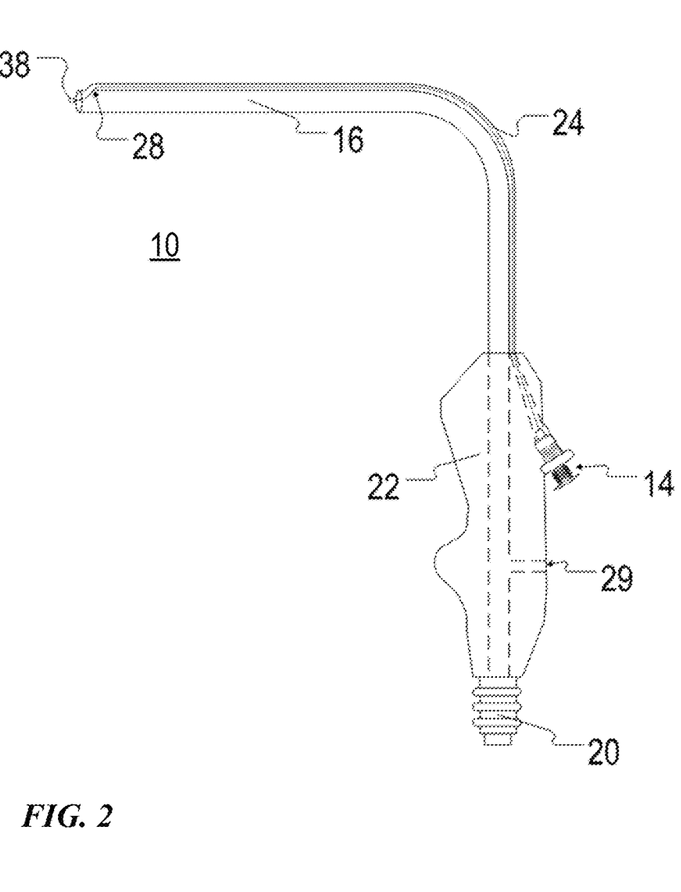
FIG. 2 is a schematic illustration of a side view of the anti-clog suction tip apparatus 10 of FIG. 1, wherein the ejection wire assembly is shown in an advanced position.
Figures 3, 4, 5:
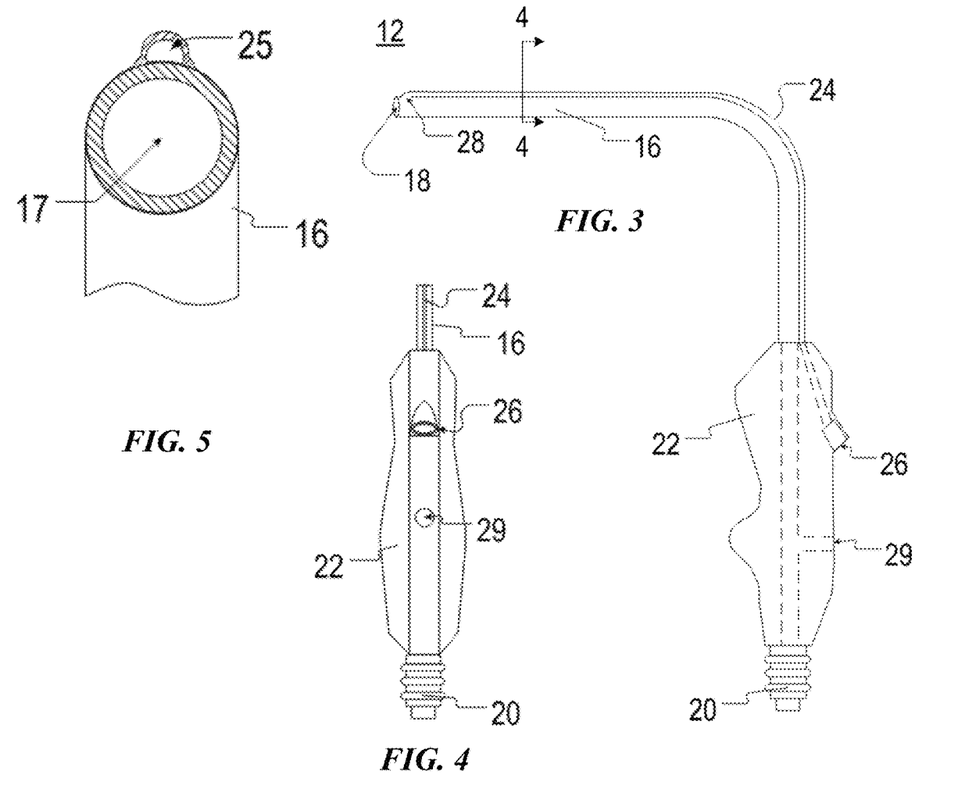
FIG. 3 is a schematic illustration of a side view of a suction tip assembly shown as part of the anti-clog suction tip apparatus 10 of FIG. 1.
FIG. 4 is a schematic illustration of a top view of the suction tip assembly of FIG. 3.
FIG. 5 is a schematic illustration of a cross-sectional view of the suction tip assembly of FIG. 3 taken along the line 4-4.
Figure 6A:
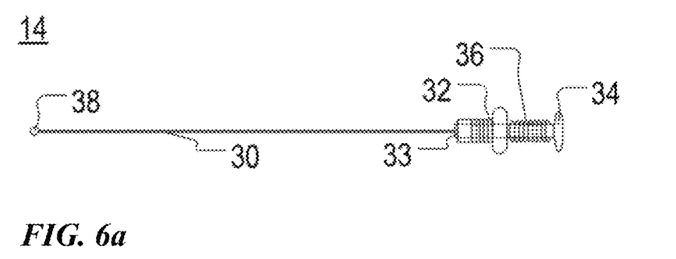
FIGS. 6a is a schematic illustration of a side view of the ejection wire assembly shown as part of the anti-clog suction tip apparatus 10 of FIG. 1, wherein the ejection wire assembly is shown in a retracted position.
Figure 6B:
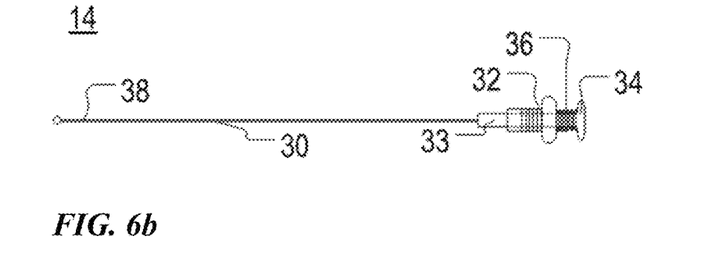
FIGS. 6b is a schematic illustration of a side view of the ejection wire assembly shown as part of the anti-clog suction tip apparatus 10 of FIG. 1, wherein the ejection wire assembly is shown in an advanced position.

FIG. 1 is a side view of a preferred anti-clog suction tip apparatus 10 in accordance with one or more aspects of the invention. FIG. 2 is a side view of the anti-clog suction tip apparatus 10 of FIG. 1. The apparatus 10 is generally comprised of a suction tip assembly 12 and a ejection wire assembly 14. FIG. 3 is a side view of the suction tip assembly 12 without the ejection wire assembly 14, and FIG. 4 is a top plan view of the suction tip assembly 12 of FIG. 3. Conversely, FIGS. 6a and 6b each includes a side view of the ejection wire assembly 14 without the suction tip assembly 12. FIG. 6a shows the ejection wire assembly in a retracted position, and FIG. 6b shows the ejection wire assembly in an advanced or extended position.

With particular reference now to FIGS. 2-4, the suction tip assembly 12 includes a suction tip 16 having a suction opening 18 at a distal end thereof and a hose attachment portion 20 at a proximal end thereof. The anti-clog suction tip apparatus 10 is adapted to attach to a hose at the hose attachment portion, with the hose having a suction source attached thereto. Suction applied through the hose is directed via a suction channel 17 through the suction tip assembly 12 to the suction opening 18 of the suction tip 16, whereby the anti-clog suction tip apparatus 10 is useful during surgical procedures for the removal of blood, tissue, and the like, from a surgical site.

The suction tip assembly 12 further includes a handle 22 and an ejection wire conduit 24 that defines at least a portion of an ejection wire channel 25 extending along the suction tip 16. Preferably, at least a portion of the ejection wire conduit 24 extends in abutment with the suction tip 16 and may be integrally formed therewith, or separately formed and adhered or otherwise attached to the suction tip 16. The ejection wire channel 25 preferably extends from a wire insertion opening 26 located on the handle 22 to a wire exit opening 28 of the ejection wire conduit 24 at the suction tip 16 proximate the suction opening 18. FIG. 5 is a schematic illustration of a cross-sectional view of the suction tip assembly 12 taken along the line 4-4 in FIG. 3 and shows the ejection wire channel 25 in relation to the suction channel 17 of the suction tip 16.

In at least one preferred embodiment, the wire insertion opening 26 is a threaded opening. Furthermore, in at least one preferred embodiment, the handle 22 includes a vacuum tunnel opening 29. Covering the vacuum tunnel opening 29 during use of the anti-clog suction tip apparatus 10 increases the vacuum pressure exerted at the suction opening 18.

As perhaps best seen in FIGS. 6a and 6b, the ejection wire assembly 14 comprises an ejection wire 30, an outer member 32, an inner member 33, an ejection button 34 (also sometimes referred to as a 'tab'), and a biasing spring 36. In one or more preferred embodiments, the ejection wire 30 comprises a semi-rigid cable extending from the inner member 33. The ejection wire 30 includes a small ball tip 38 at the end thereof to prevent unintended injury during use.

Furthermore, a first end of the inner member 33 preferably is integrally formed with the ejection button 34 and a second end of the inner member 33 is attached to the ejection wire 30. The outer member 32 also encompasses at least a portion the inner member 33 (shown in dotted lines), and the biasing spring 36 encircles a portion of the inner member 33 and is configured to bias the ejection button 34 away from the outer member 32 toward the retracted position shown in FIG. 6a.

In some alternative embodiments, the ejection button is formed separately from and is connected to the ejection wire by an inner member or other element.

As seen best in FIG. 6b, assuming the outer member 32 is immobile, as force is applied to the ejection button 34, the ejection button 34, the inner member 33, and the ejection wire 30 advance in the direction of the applied force and the biasing spring 36 contracts. Upon removal of the force, the biasing spring 36 returns to its relaxed position, forcing the ejection button 34, the inner member 33 and the ejection wire 30 back to the retracted position of FIG. 6a.

Returning now to FIG. 1, the ejection wire assembly 14 is shown threadably attached to the suction tip assembly 12 and in a retraced position. To affix to the ejection wire assembly 14 to the suction tip assembly 12, the ejection wire 30 is first inserted into the wire insertion opening 26 on the handle. Next, the ejection wire 30 is slid forward to occupy the ejection wire channel 25. Preferably, only upon full insertion of the ejection wire 30 into the ejection wire channel 25 can the outer member 32 be threadably secured to the cable insertion opening 26 in the handle 22.

As discussed previously with reference to FIGS. 6a and 6b, the ejection wire assembly 14 is placed in an advanced position by applying force to the ejection button 34. As force is applied, the ejection wire 30 moves forward. When the ejection wire 30 is advanced forward, the ball tip 38 passes through the wire exit opening 28 into the suction tip 16 and dislodges any biological debris clogging the suction tip 16, such as blood, tissue, and the like, to unclog the suction tip 16. Such debris may be expelled through the through the suction opening 18. In at least one preferred embodiment, the ball tip 38 does not extend more than 3 millimeters beyond (protract from) the suction opening 18 when the ejection wire 30 is fully advanced by depression of the ejection button 34.

Preferably, the anti-clog suction tip apparatus 10 is provided in a sterile packaging for use in a surgical environment. The packaging may include vacuum packaging of the anti-clog suction tip apparatus 10, or any or all of the components thereof, in a sterile manner. The sterile packaging in which the anti-clog suction tip apparatus 10 is provided is opened by sterile technique in the surgical environment, and the anti-clog suction tip apparatus 10 is removed from the packaging and placed on a sterile table to await use by a surgeon or surgical assistant. A hose attached to a suction source is secured to the hose attachment portion 20. Upon activation of the suction source, a vacuum is produced within the suction tip 16, enabling the suction tip 16 to be used for removing biological debris, such as blood, tissue, and the like, from the operation site.

During the course of use, it is believed that the suction tip 16 is likely to become clogged with biological debris. Immediate ejection of the debris is oftentimes necessary in the surgical environment. To remove unwanted debris from the suction tip 16, the user applies force to the ejection button 34, causing the ejection wire 30 to advance within the ejection wire conduit 24 through the wire exit opening 28 and into the suction channel 17 within the suction tip 16, thereby expelling through the suction opening 18 any debris that may be clogged in the suction tip 16. Some debris that is dislodges also may be suctioned through the suction tip 16. To retract the ejection wire 30, the user removes the applied force from the ejection button 34. The biasing spring 36 causes the ejection button 34 to return to its initial position, thus retracting the ejection wire 30. When retracted, the ejection wire 30, and in particular the ball tip 38, is retained within the ejection wire channel 25 and does not obstruct normal suctioning of the debris during use of the apparatus 10.

In one or more preferred embodiments, the anti-clog suction tip apparatus 10 is intended to be disposed after a single surgical use. After use, the anti-clog suction tip apparatus 10 will include biological and potentially hazardous debris, and thus, should be disposed according to any applicable HAZMAT protocol.

In at least one preferred embodiment, a secondary wire is supplied to be inserted into the suction tip 16 through the suction opening 18 to more completely clear debris if the ejection wire 30 is unable to completely expel the debris. It is further contemplated that alternative ejection wires may be included that have different sizes, dimensions, and tip profiles, and that have wires of different diameters and different rigidity characteristics. Section of a particular ejection wire can be made in accordance with surgeon preference.

As previously mentioned, the ejection wire assembly 14 is shown secured to the suction tip assembly 12 to for the apparatus 10, and is disposed in a retracted position, in FIG. 1. In contrast, the ejection wire assembly 14 is shown deployed in an advanced position in FIG. 2. FIGS. 6a and 6b are side views of the ejection wire assembly 14 wherein ejection wire assembly 14 in a retracted position in FIG. 6a and in an advanced position in FIG. 6b.

Additional preferred embodiments of anti-clog suction tip apparatus in accordance with one or more aspects of the invention are shown in the remaining figures. In particular, FIGS. 7-16 show views of another anti-clog suction tip apparatus and components in accordance with one or more aspects of the invention; FIGS. 17-30 show views of another anti-clog suction tip apparatus and components in accordance with one or more aspects of the invention; FIGS. 30-48 show views of another anti-clog suction tip apparatus and components in accordance with one or more aspects of the invention; FIG. 49 shows bodies three of the anti-clog suction tip apparatus of FIGS. 7-48; and FIG. 50-60 show views of another anti-clog suction tip apparatus and components in accordance with one or more aspects of the invention.

Figures 7, 8, 9, 10, 11, 12, 13, 14:
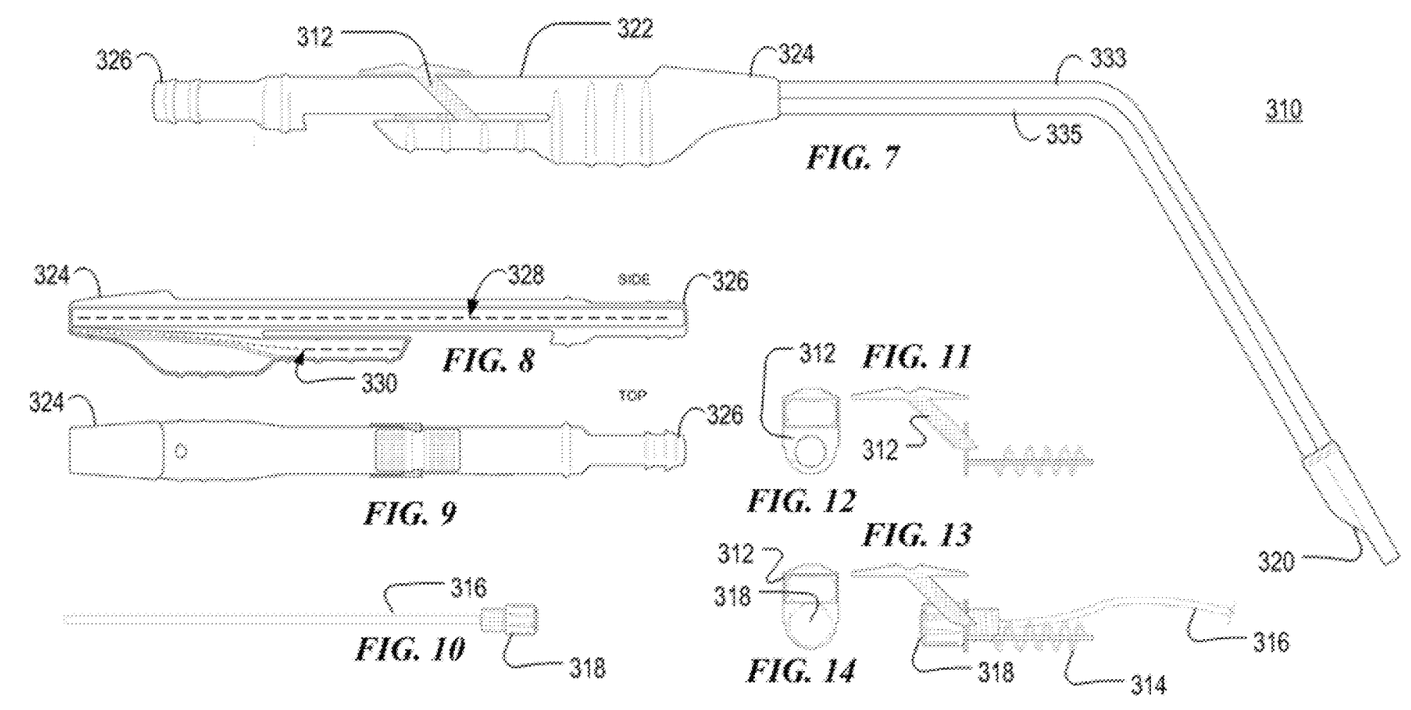
FIGS. 7-16 schematically illustrate another preferred anti-clog suction tip apparatus 310, and components thereof, in accordance with one or more aspects of the invention.

With reference first to FIGS. 7-16, FIG. 7 is a schematic illustration of a side view of a preferred anti-clog suction tip apparatus 310 in accordance with one or more aspects of the invention. Various components of the anti-clog suction tip apparatus 310 of FIG. 7 are shown in FIGS. 8-16. The apparatus 310 includes a slider 312, springs 314, stylet 316, screw cap 318, conversion tip 320, and body 322. The slider 312, spring 314, stylet 316, a screw cap 318, and conversion tip 320 are intended to be disposable after use in a single operation. The body 322 is intended to be autoclaved and, thus, available for use in multiple operations. The body 322 includes a forward end portion 324 and back end portion 326. A suction neck 333 and a stylet neck 335 generally coextend from the body 322, with a vacuum passage extending through the suction neck 333 to the tip 320, and with a stylet passage extending through the stylet neck 335 to the tip 320. It will be appreciated that the ventral side of the suction neck 333 abuts the dorsal side of the stylet neck 335. A side cross-sectional view of the body 322 is shown in FIG. 8, which reveals the suction passage 328 and stylet passage 330 that extend through the body 322. A top view of the body 322 and slider mechanism 312 is shown in FIG. 9. The stylet 316 and screw cap 318 are shown in FIG. 10. The slider mechanism 312, which includes two parallel posts with springs, is shown in FIG. 11 from a side thereof, and is shown in FIG. 12 from the back looking forward. Similarly, the slider mechanism 312 is shown in FIG. 13 from a side thereof, wherein the stylet 316 and screw cap 318 have been attached in threading engagement therewith, and also is shown in FIG. 14 from the back looking forward.

Figures 15, 16:
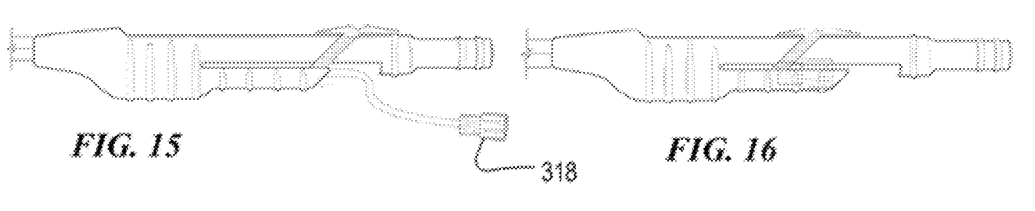

Steps for inserting the stylet and screw cap and otherwise making the apparatus 310 ready for use are shown in FIGS. 10, 15, and 16. The steps include removing the stylet 316 and the screw cap 318 (preferably pre-attached) from a sterile package (represented by FIG. 10); pushing the slider mechanism 312 toward the back end portion 326 of the body 322 and inserting the stylet 318 through an opening in the slider mechanism 312 into the stylet cavity of the body 322 (FIG. 15); and securing the stylet 316 to the slider mechanism 312 by screwing the screw cap 318 into threading engagement with the slider mechanism 312 (FIG. 16).

Figures 17, 18, 19, 20, 21, 22, 23, 24, 25:
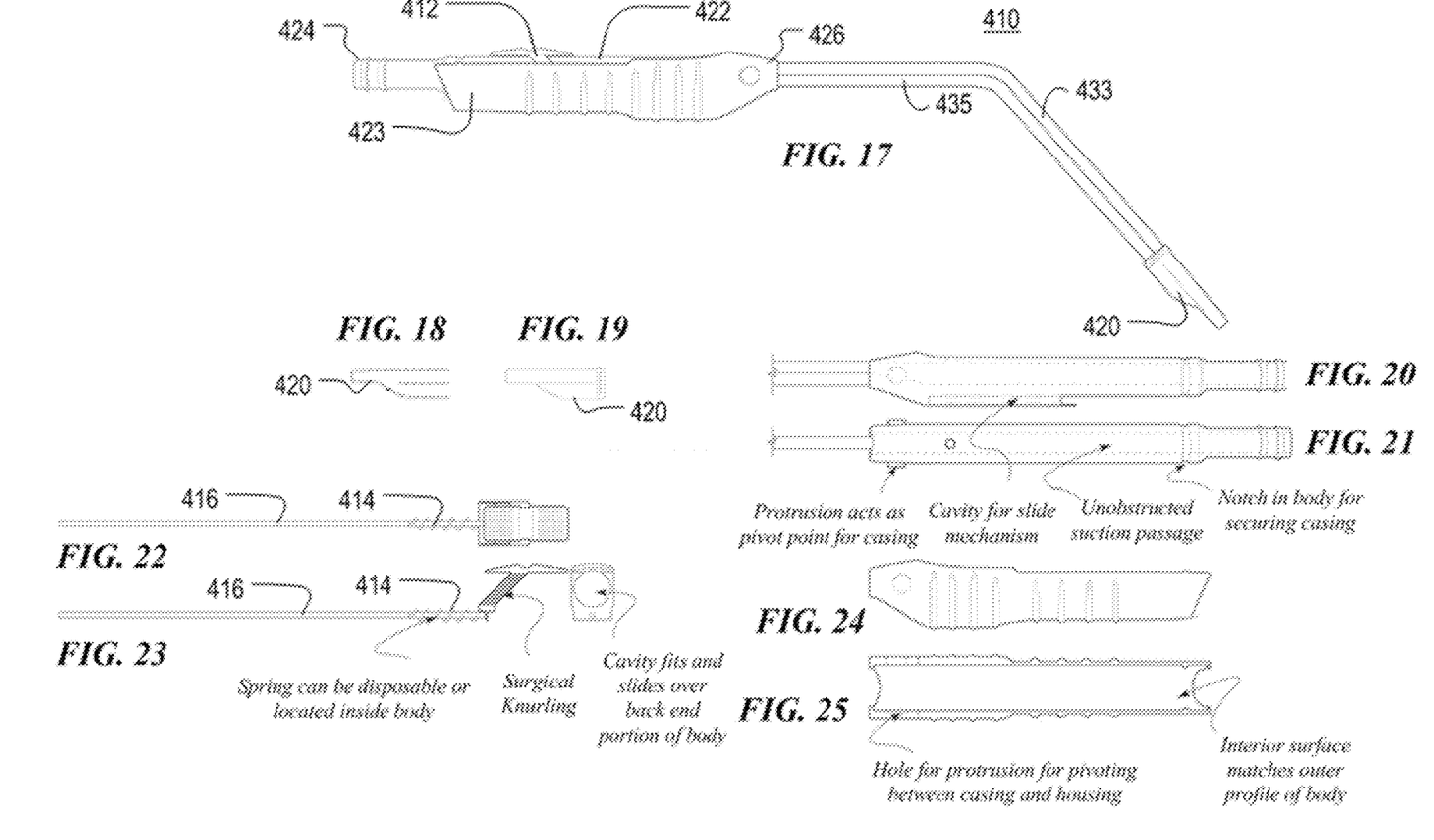
FIGS. 17-25 schematically illustrate another preferred anti-clog suction tip apparatus 410, and components thereof, in accordance with one or more aspects of the invention.

With reference first to FIGS. 17-29, another anti-clog suction tip apparatus 410 is shown in FIG. 17 and various components thereof are shown in FIGS. 18-29. The apparatus 410 includes a slider 412, spring 414, stylet 416, tip 420, and body 422 and casing 423. The slider 412, spring 414, stylet 416, and tip 420 are intended to be disposable after use in a single operation. The body 422 and casing 423 are intended to be autoclaved and, thus, available for use in multiple operations. The body 422 includes a forward end portion 424 and back end portion 426. A suction neck 433 and a stylet neck 435 generally coextend from the body 422, with a vacuum passage extending through the suction neck 433 to the tip 420, and with a stylet passage extending through the stylet neck 435 to the tip 420. It will be appreciated that the ventral side of the suction neck 433 abuts the dorsal side of the stylet neck 435. A side cross-sectional view of the tip 420 is shown in FIG. 18, which reveals the merger of the stylet passage and the suction passage within the tip 420; and a side view of the tip 420 is shown in FIG. 19. A top view of the body 422 is shown in FIG. 20; and a top view of the body 422 is shown in FIG. 21. The slider 412, spring 414, and stylet 416 are shown in FIG. 22 from the top, and in FIG. 23 from the side. A side view of the casing 423 is shown in FIG. 24; and a top view of the casing 423 is shown in FIG. 25. The casing removably attaches to the body 422 and, when the casing 423 is attached, partially surrounds and encases the body 422.

Figures 26, 27, 28, 29, 30:
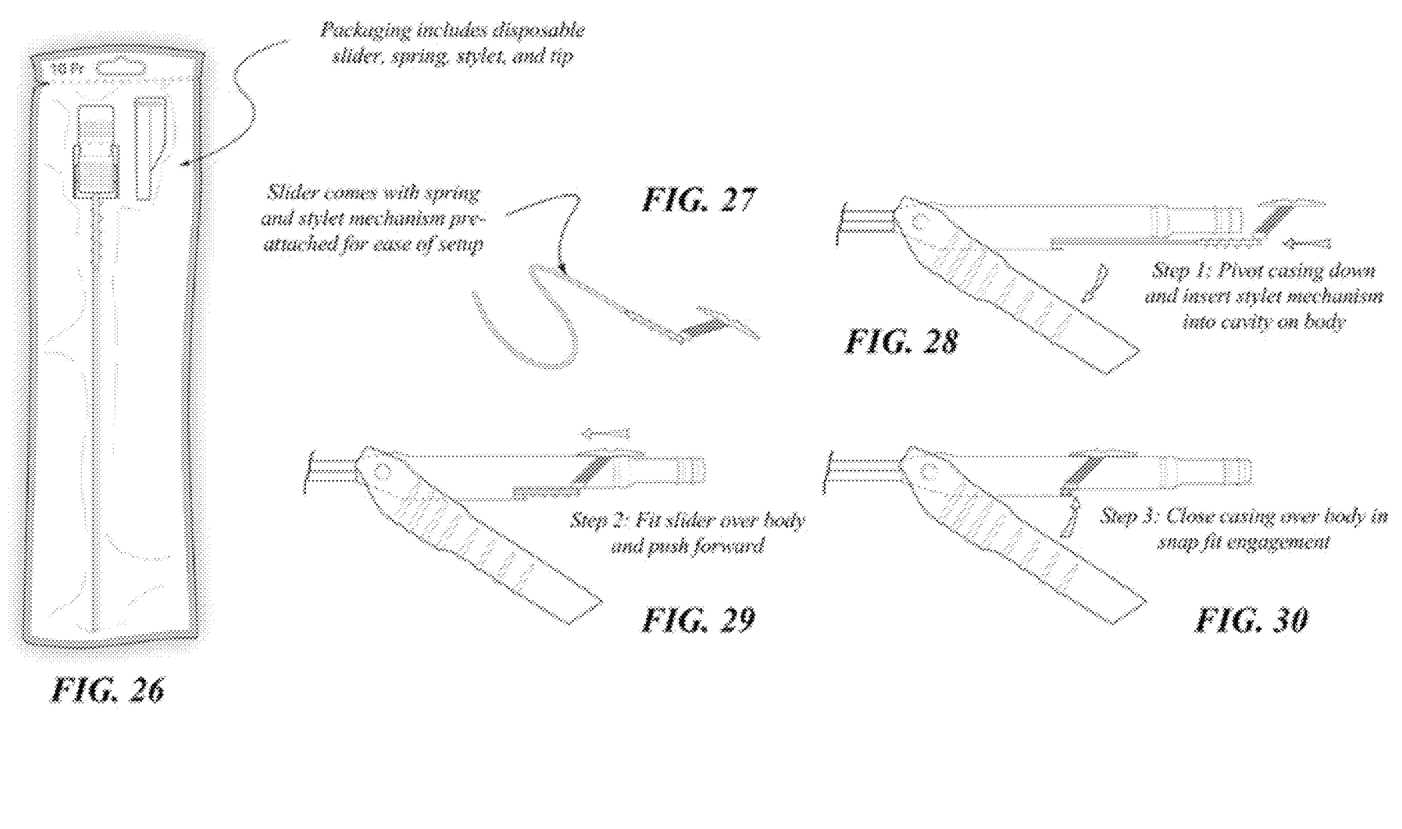
FIG. 26 illustrate the packaging of disposable slider, spring, stylet, and tip, with respect to the preferred embodiment of FIGS. 17-25.
FIGS. 27-30 illustrate steps of assembling the apparatus 410 using the disposable components of FIG. 26.

Steps for installing the disposable components and otherwise making the apparatus 410 ready for use are shown in FIGS. 27-30. The steps include removing the slider 412, spring 414, and stylet 416 components from the sterile package shown in FIG. 26, which components come pre-attached as shown in FIG. 27; pivoting the casing 423 downwardly away from the body 422 and inserting the stylet 416 into the cavity of the body 422, as shown in FIG. 28; and fitting and sliding the slider 412 over the body 422, pushing it forward as shown in FIG. 29; and closing the casing 423 back onto the body 422 in snap fit engagement as shown in FIG. 30.

Figures 31, 32, 33, 34, 35, 36, 37, 38, 39, 40, 41, 42, 43:
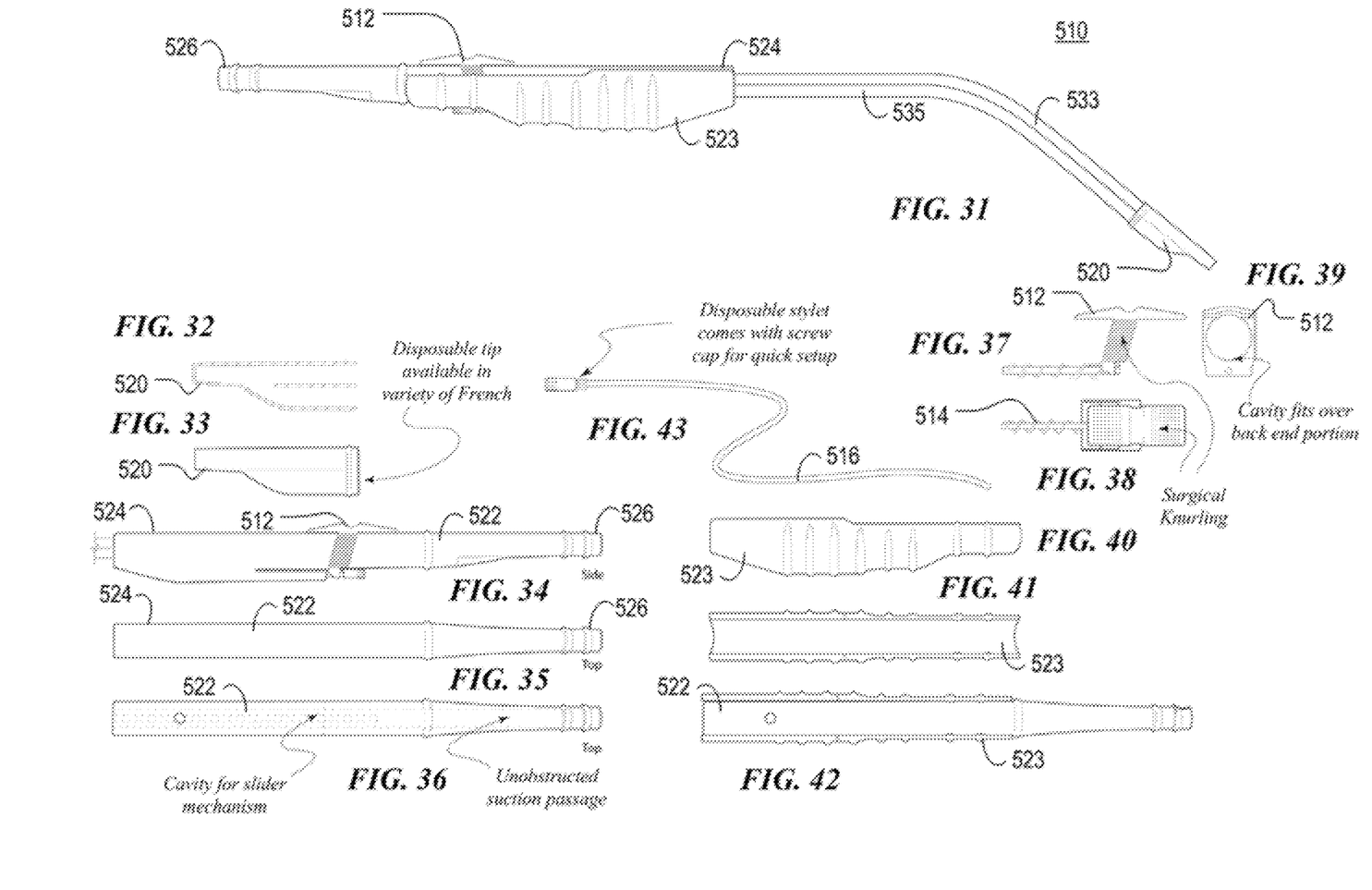
FIGS. 31-43 schematically illustrate another preferred anti-clog suction tip apparatus 510, and components thereof, in accordance with one or more aspects of the invention.

With reference first to FIGS. 31-43, another anti-clog suction tip apparatus 510 is shown in FIG. 31 and various components thereof are shown in FIGS. 32-43. The apparatus 510 includes a slider 512, spring 514, stylet 516 with included screw head, tip 520, and body 522. The stylet 516 and tip 520 are intended to be disposable after use in a single operation. They stylet 516 is shown in FIG. 43. The slider 512, spring 514, and body 522 are intended to be autoclaved and, thus, available for use in multiple operations. Indeed, these components are preferably press-fit together at the point of manufacture. The body 522 includes a forward end portion 524 and back end portion 526. A casing 523 including a handle grip portion is also provided that is removably attached to the body 522. A suction neck 533 and a stylet neck 535 generally coextend from the body 522, with a vacuum passage extending through the suction neck 533 to the tip 520, and with a stylet passage extending through the stylet neck 535 to the tip 520. It will be appreciated that the ventral side of the suction neck 533 abuts the dorsal side of the stylet neck 535. A side cross-sectional view of the tip 520 is shown in FIG. 32, which reveals the merger of the stylet passage and the suction passage within the tip 520; and a side view of the tip 520 is shown in FIG. 33. A side view of the body 522 is shown in FIG. 34; and top views of the body 522 are shown in FIGS. 35 and 36. The slider 512 and spring 514 are shown in FIG. 37 from the top; in FIG. 38 from the side; and back view looking forward in FIG. 39. A side view of the casing 523 is shown in FIG. 40; and a top view of the casing 523 is shown in FIG. 41. The casing removably attaches to the body 522 and, when the casing 523 is attached, partially surrounds and encases the body 522 and defines a handle grip for the apparatus 510. A top view of the body 522 and casing 523 is shown in FIG. 42.

Figures 44, 45, 47:
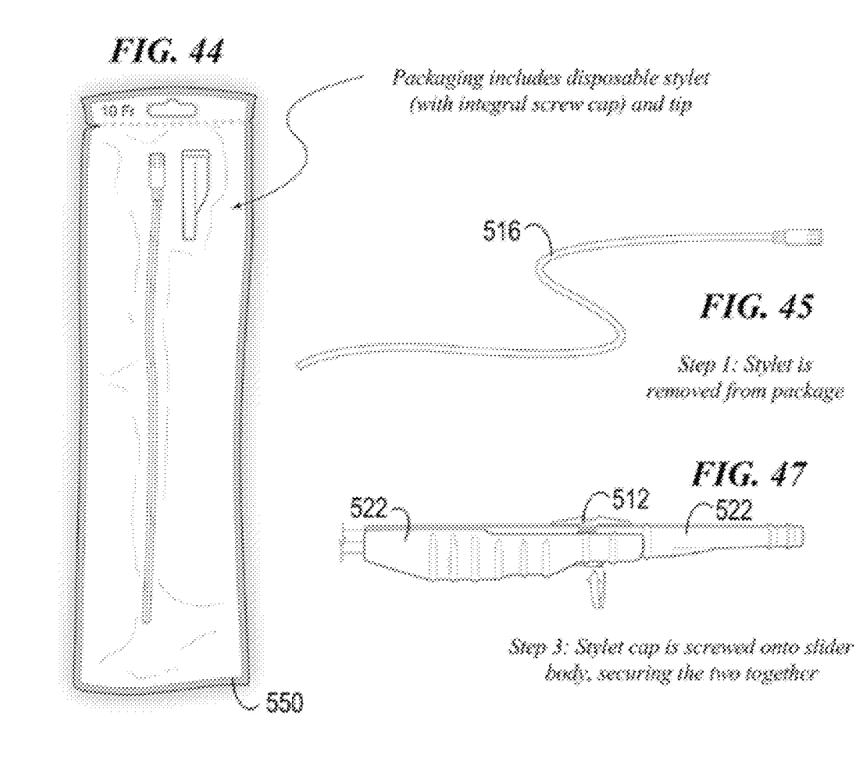
FIG. 44 illustrate the packaging of a disposable stylet with integral screw cap and tip, with respect to the preferred embodiment of FIGS. 31-43.
FIGS. 45-48 illustrate steps of assembling the apparatus 510 using the disposable components of FIG. 44.
Figure 46:
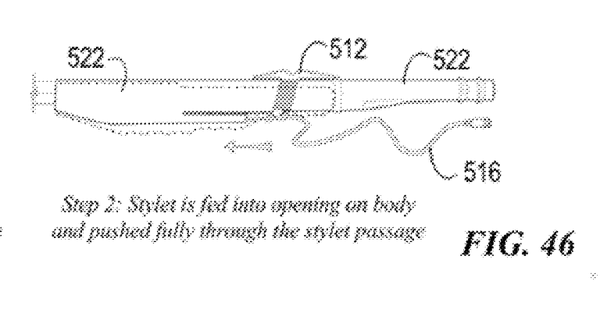
Figure 48:
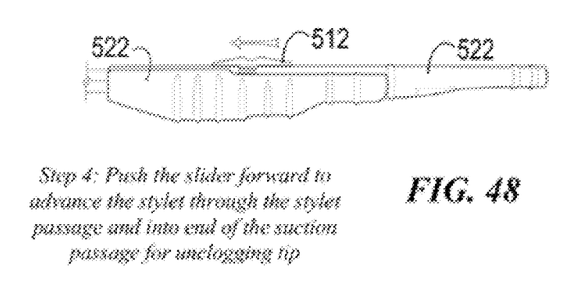
Figure 49:
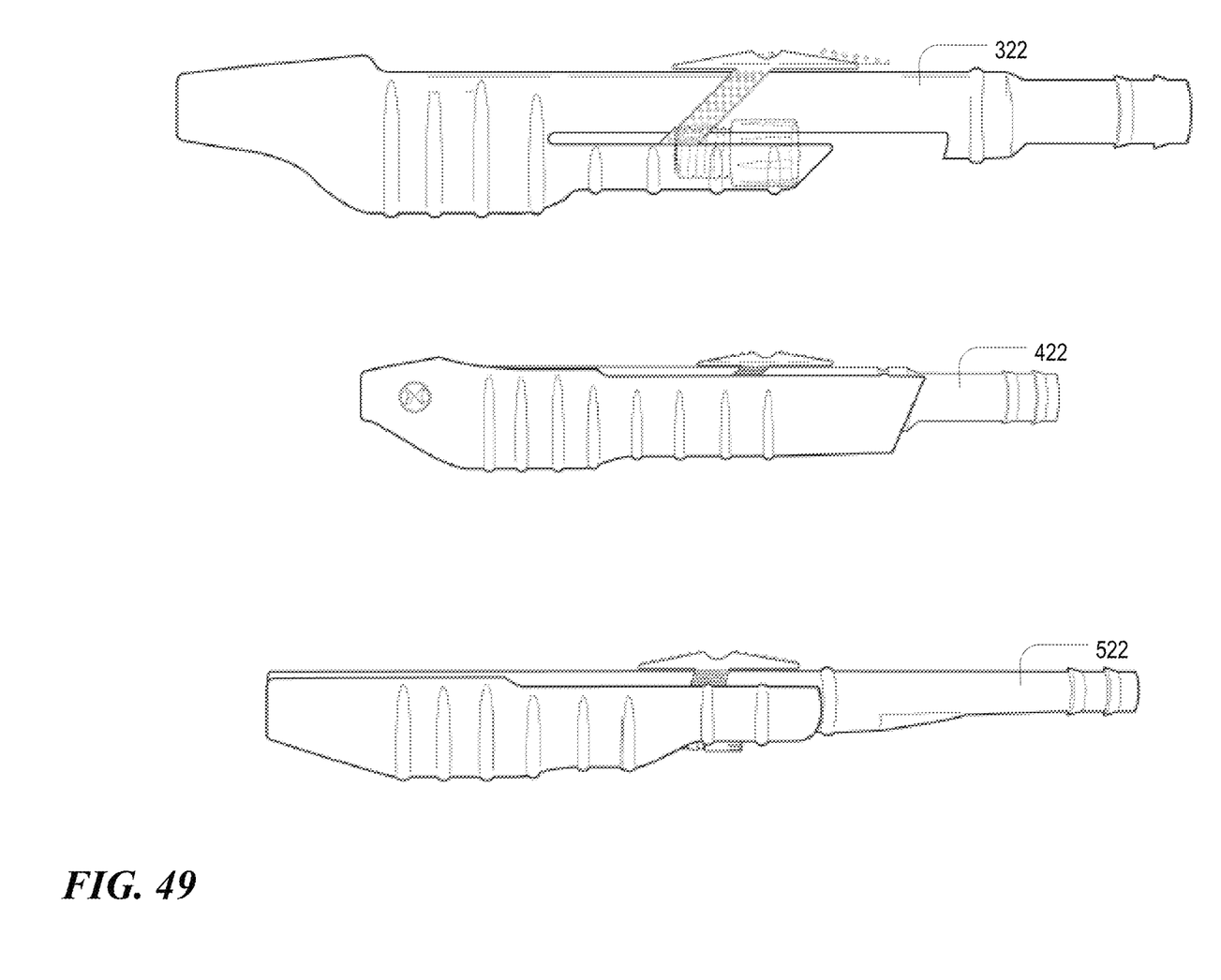
FIG. 49 illustrates contemplated relative size relations between the three bodies 322,422,522.

Steps for installing the disposable components and otherwise making the apparatus 510 ready for use are shown in FIGS. 45-48. The steps include removing the stylet 516 with screw head from a sterile package 550 (shown in FIG. 44), which step is represented in FIG. 45; inserting the stylet 516 into the cavity of the body 522, as shown in FIG. 46; securing the stylet to the slider by screwing the head of the stylet into a threaded opening of the slider, as represented in FIG. 47; and pushing the slider 512 forward to advance the stylet 516 through the stylet passage and into the suction passage for dislodging debris when using the apparatus 510, as represented in FIG. 48.

As represented in FIG. 49, it is contemplated that body 322 is the largest of the three bodies 322,422,522; body 522 is of relative intermediate size; and body 422 is the smallest of the three bodies 322,422,522.

Figures 50, 51, 52, 53, 54, 55, 56, 57, 58:
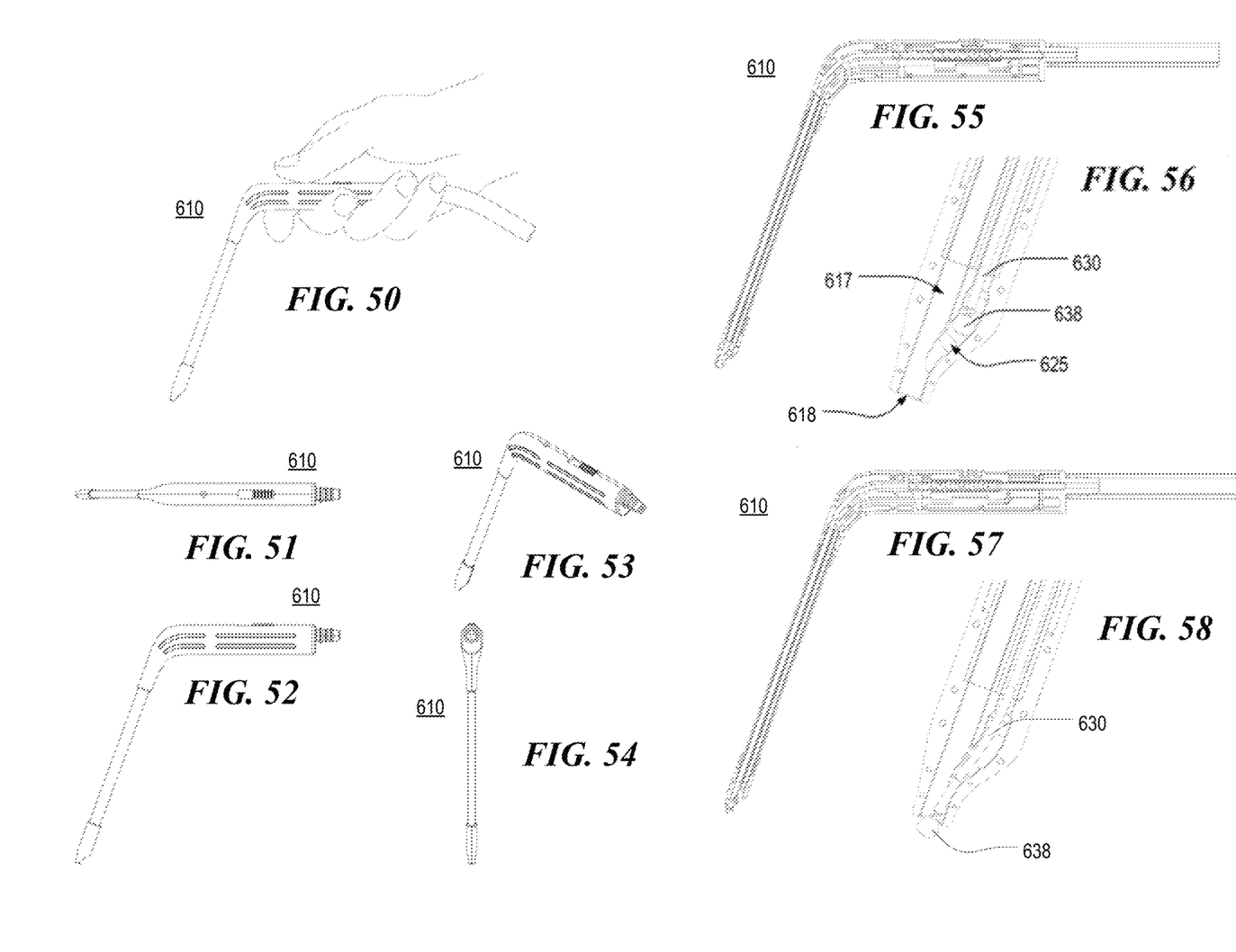
FIG. 50 schematically illustrates yet another preferred embodiment of an anti-clog suction tip apparatus 610 in accordance with one or more aspects of the invention, shown being held in hand for use by a healthcare professional.
FIG. 51 schematically illustrates a top view of the apparatus 610 of FIG. 50.
FIG. 52 schematically illustrates a side elevational view of the apparatus 610 of FIG. 50.
FIG. 53 schematically illustrates a perspective view of the apparatus 610 of FIG. 50.
FIG. 54 schematically illustrates a back elevational view of the apparatus 610 of FIG. 50.
FIG. 55 schematically illustrates in cross-section a side elevational view of the apparatus 610 of FIG. 50, wherein the ejection wire assembly is not deployed.
FIG. 56 schematically illustrates an enlarged view of the distal end of the suction tip of the apparatus 610 of FIG. 55, showing the location of the tip of the ejection wire assembly received completely within the ejection wire channel.
FIG. 57 schematically illustrates in cross-section a side elevational view of the apparatus 610 of FIG. 50, wherein the ejection wire assembly is deployed.
FIG. 58 schematically illustrates an enlarged view of the distal end of the suction tip of the apparatus 610 of FIG. 57, showing the location of the tip of the ejection wire assembly extending from the ejection wire channel, through the suction channel, and out of the suction opening.

FIG. 50 schematically illustrates yet another preferred embodiment of an anti-clog suction tip apparatus 610 in accordance with one or more aspects of the invention, shown being held in hand for use by a healthcare professional. FIG. 51 schematically illustrates a top view of the apparatus 610 of FIG. 50; FIG. 52 schematically illustrates a side elevational view of the apparatus 610 of FIG. 50; FIG. 53 schematically illustrates a perspective view of the apparatus 610 of FIG. 50; and FIG. 54 schematically illustrates a back elevational view of the apparatus 610 of FIG. 50.

Additionally, FIG. 55 schematically illustrates in cross-section a side elevational view of the apparatus 610 of FIG. 50, wherein the ejection wire assembly is not deployed; and FIG. 56 schematically illustrates an enlarged view of the distal end of the suction tip of the apparatus 610 of FIG. 55, showing the location of the tip of the ejection wire assembly received completely within the ejection wire channel. In contrast, FIG. 57 schematically illustrates in cross-section a side elevational view of the apparatus 610 of FIG. 50, wherein the ejection wire assembly is deployed; and FIG. 58 schematically illustrates an enlarged view of the distal end of the suction tip of the apparatus 610 of FIG. 57, showing the location of the tip of the ejection wire assembly extending from the ejection wire channel, through the suction channel, and out of the suction opening.

Figures 59, 60:
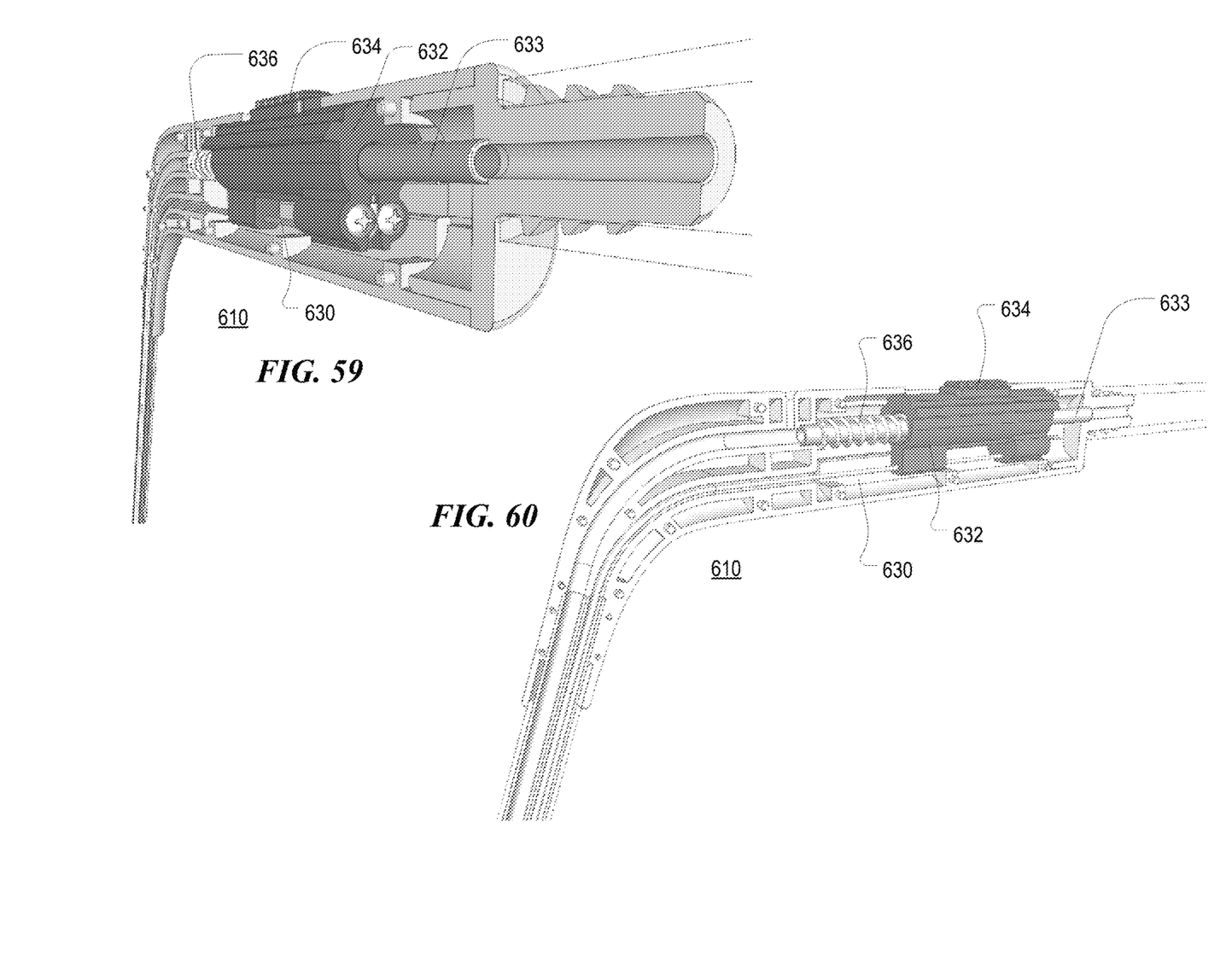
FIG. 59 schematically illustrates a perspective rear view, in cross-section, of the apparatus 610 of FIG. 50.
FIG. 60 schematically illustrates a perspective front view, in cross-section, of the apparatus 610 of FIG. 50.

FIG. 59 schematically illustrates a perspective rear view, in cross-section, of the apparatus 610 of FIG. 50. FIG. 60 schematically illustrates a perspective front view, in cross-section, of the apparatus 610 of FIG. 50.

The anti-clog suction tip apparatus 610 is similar in structure, operation and use to apparatus and methods previously described herein. In this respect, the apparatus 610 includes a ejection wire assembly comprising an ejection wire 630, an outer member 632, an inner member 633, an ejection button 634 (also sometimes referred to as a 'tab' or 'slider'), and a biasing spring 636. The ejection wire preferably is a semi-rigid cable and, in apparatus 610, the ejection wire is attached to the outer member (which slides relative to the inner member 633 comprising a fixed shaft). Moreover, the ejection button 634 is part of the outer member 632 and, preferably, is injection molded or otherwise integrally formed therewith. The ejection wire 630 includes a small ball tip 638 at the end thereof to prevent unintended injury during use, as well as to provide an enlarged end for clearing of the suction channel when the ball tip is deployed. When deployed, the ball tip extends through the suction channel 617 and out of the suction opening 618 for dislodging debris. When not deployed, the ball tip rests within the ejection wire channel 625.

Most of the components of apparatus 610 preferably are formed from conventional molding processes from ABS (medical grade) Cycolac HMG94MD resin, or equivalent. The ball tip preferably comprises a plunger ball made of nylon or stainless steel, preferably includes an opening extending therethrough, and is physically attached by swaging at the end of the ejection wire. The ejection wire preferably is made from 302 stainless steel, or equivalent. The overall weight of the apparatus 610 preferably is approximately 0.8 ounces.

A perceived advantage of one or more preferred anti-clog suction tip apparatus disclosed herein is the location of the ejection wire assembly out of a user's line of sight so as not to obstruct the user's view during a surgical procedure.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A suction tip apparatus, comprising:
   (a) an ejection wire located within a stylet passage, which stylet passage opens into a suction channel of the suction tip apparatus;
   (b) an inner member comprising a shaft defining part of the suction channel;
   (c) an outer member extending around and mounted on the inner member for sliding movement along the inner member, the ejection wire being connected to the outer member for movement concurrent with sliding of the outer member on the inner member; and
   (d) a slider that is part of the outer member and accessible on an exterior of the suction tip apparatus, the slider being manually operable to slide the outer member on the inner member and move the ejection wire within the stylet passage toward a suction opening of the suction channel.

2. The suction tip apparatus of claim 1, further comprising a biasing spring biasing the outer member in its slidable disposition over the inner member.

3. The suction tip apparatus of claim 1, further comprising a handle portion, wherein the handle portion defines a vacuum tunnel having a vacuum tunnel opening located on a side of the handle portion, on which side the slider is accessible.

4. The suction tip apparatus of claim 3, wherein the vacuum tunnel opening is located on a top side of the suction tip apparatus.

5. The suction tip apparatus of claim 3, wherein the vacuum tunnel opens into the suction channel proximate a distal end of the shaft.

6. The suction tip apparatus of claim 1, further comprising a handle portion, wherein the inner member is located within an interior of the handle portion.

7. The suction tip apparatus of claim 6, further comprising a biasing spring biasing the outer member in its slidable disposition over the inner member.

8. The suction tip apparatus of claim 7, wherein the spring extends around the shaft.

9. A method of clearing debris from a surgical site, comprising the steps of:
   (a) attaching a suction tip apparatus to a suction source for the removal of debris through suction applied at a suction opening of a suction tip of the suction tip apparatus, the suction tip apparatus comprising,
      (i) an ejection wire located within a stylet passage, which stylet passage opens into the suction channel of the suction tip apparatus,
      (ii) an inner member comprising a shaft defining part of the suction channel,
      (iii) an outer member extending around and mounted on the inner member for sliding movement along the inner member, the ejection wire being connected to the outer member for movement concurrent with sliding of the outer member on the inner member, and
      (iv) a slider that is part of to the outer member and accessible on an exterior of the suction tip apparatus, the slider being manually operable to slide the outer member on the inner member and move the ejection wire within the stylet passage toward the suction opening of the suction channel;
   (b) activating the suction source for applying suction at the suction opening of the suction tip;
   (c) placing the suction tip near the debris causing the debris to be suctioned into the suction opening of the suction tip; and
   (d) transitioning the ejection wire, whereby debris clogging the suction tip may be expelled from the suction opening.

10. The method of claim 9, further comprising biasing the outer member in its slidable disposition over the inner member with a spring.

11. The method of claim 10, wherein the spring extends around the shaft.

12. The method of claim 9, further comprising a handle portion, wherein the handle portion defines a vacuum tunnel having a vacuum tunnel opening located on a side of the handle portion, on which side the slider is accessible.

13. The method of claim 12, wherein the vacuum tunnel opening is located on a top side of the suction tip apparatus.

14. The method of claim 12, wherein the vacuum tunnel opens into the suction channel proximate a distal end of the shaft.

15. The method of claim 9, further comprising a handle portion, wherein the inner member is located within an interior of the handle portion.

16. The method of claim 15, further comprising biasing the outer member in its slidable disposition over the inner member with a spring.

17. The method of claim 16, wherein the spring extends around the shaft.

\* \* \* \* \*